United States Patent [19]

Suzuki et al.

[11] 4,107,014
[45] Aug. 15, 1978

[54] ISOELECTRIC POINT MARKERS FOR GEL ISOELECTRIC SEPARATION

[75] Inventors: Yasuo Suzuki, Suita; Isamu Takagahara, Kawanishi; Tsuyoshi Fujita; Katsumi Fujii, both of Suita; Takekazu Horio, Takatsuki, all of Japan

[73] Assignee: Oriental Yeast Co. Ltd., Japan

[21] Appl. No.: 754,976

[22] Filed: Dec. 28, 1976

[30] Foreign Application Priority Data

Jan. 30, 1976 [JP] Japan .................................. 51/8388

[51] Int. Cl.$^2$ ........................................... G01N 27/26
[52] U.S. Cl. ........................ 204/180 R; 204/299 R; 424/12; 260/112 R; 260/112 B
[58] Field of Search ............... 204/180 G, 180 R, 299; 23/230 B; 424/12; 260/102, 112 R, 112 B

[56] References Cited

U.S. PATENT DOCUMENTS

| | | | |
|---|---|---|---|
| 3,616,456 | 10/1971 | Valmet | 204/299 |
| 3,770,603 | 11/1973 | Grubhofer et al. | 204/299 X |
| 3,901,780 | 8/1975 | Denckla | 204/299 X |
| 4,030,995 | 6/1977 | Starkweather | 204/299 R X |

*Primary Examiner*—Arthur C. Prescott
*Attorney, Agent, or Firm*—Stevens, Davis, Miller & Mosher

[57] ABSTRACT

Isoelectric point markers for a gel isoelectric separation are prepared to comprise at least two colored proteins of which the isoelectric point pHs are known and wherein the difference between the highest value and the lowest value among the said pHs is not less than 0.5. The markers are applied to analyze proteins in a gel isoelectric separation method. The method employing the said markers makes it easy to analyze proteins and shows an excellent performance.

6 Claims, 2 Drawing Figures

ISOELECTRIC POINT MARKERS FOR GEL ISOELECTRIC SEPARATION

BACKGROUND OF THE INVENTION

The invention relates to isoelectric point markers and a gel isoelectric separation method by employing isoelectric point markers. More particularly this invention relates to a gel isoelectric separation method for measuring the isoelectric point of proteins by employing a combination of colored proteins of which the isoelectric points are known.

Recently, in the fields of biochemistry and clinical diagnosis a gel isoelectric separation method (also named a gel isoelectric focusing method) has been taken note of as a method for separating, purifying and analyzing proteins. This method is considered to be a simplified method of the density gradient isoelectric separation method, which was developed by Svensson et al. When a mixture of special ampholytes having different isoelectric points at different pH values is in a gel such as acrylamide and agar-agar, and an electric current is applied between both ends of the gel, a pH gradient derived from the ampholytes is developed between the electrodes placed at both ends. This method is based on the principle that under the influence of an electric field, proteins are focused at their own isoelectric points in the pH gradient. (C. W. Wringley : Method in Enzymology, Vol. 22, page 559–564, Academic Press) According to this invention, it is possible not only to separate and purify proteins by utilizing the differences among the isoelectric points of the proteins, but also to determine isoelectric points of proteins by measuring the pH gradient in a gel. Therefore, this method is very useful as a method of analyzing proteins.

There, however, are some disadvantages in this method. One disadvantage is that a complicated operation is required in determining the pH gradient formed in a gel as described below. As soon as electrophoresis ends, the gel is removed rapidly and sliced as thinly as possible at equal intervals. Thereafter ampholytes enclosed in the resulting sliced gel intervals are extracted with pure and decarbonated water and then each pH value of the extract is measured. In this pH determination, it takes time to extract ampholytes and it is difficult to slice the gel accurately at equal intervals without failure. Furthermore, the resulting pH values vary with the conditions of extraction. Therefore this method is not applicable as a practical method. Hence, there are reported some modified methods, such as a method wherein amphoteric dyes are used together with samples as pH indicators in a gel isoelectric separation method (A. Conway-Jacobs and L. M. Lewin : Analytical Biochemistry, Vol. 43, page 394–400(1971)), and a method wherein phenanthroline-iron complexes are used for the same purpose. These methods, however, that the disadvantages that the compounds used are diffused rapidly because they are low molecular compounds and they do not focus sharply because the ionization constants of the ionized groups at opposite ends of the compounds are greatly different from each other.

SUMMARY OF THE INVENTION

It is an object of this invention to provide isoelectric point markers for a gel isoelectric separation method, which comprise at least two colored proteins of which the isoelectric point pHs are known, and the difference between the highest value and the lowest value among said pHs is not less than 0.5.

It is another object of this invention to provide a gel isoelectric separation method for the analysis of proteins by using isoelectric point markers which comprise at least two colored proteins of which the isoelectric point pHs are known and wherein the difference between the highest value and the lowest value among said pHs is not less than 0.5, and wherein the migration distances of the said markers are used as indicators of pH value.

PREFERRED EMBODIMENT OF THE INVENTION

Figure 1:
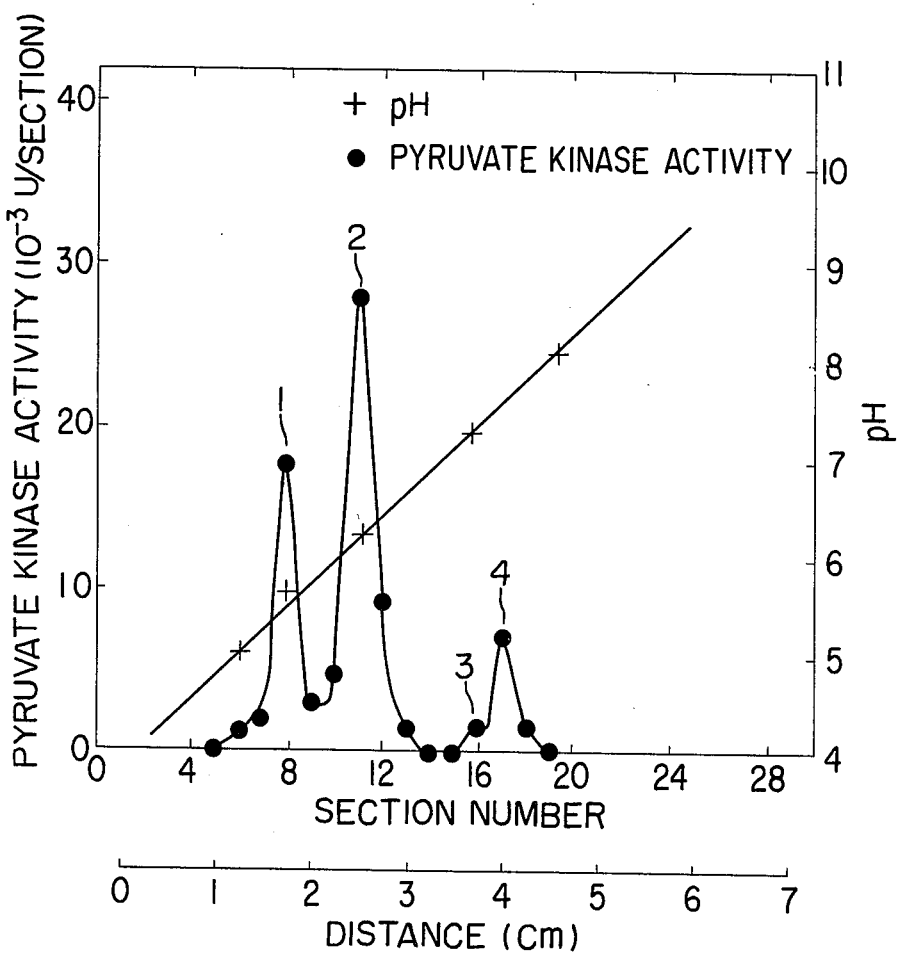
FIG. 1 is a chart showing the result obtained by using the isoelectric point markers of this invention in a gel isoelectric separation.

According to this invention, colored proteins which may be used as a marker include cytochrome-cs, myoglobins, hemoglobins, flavoproteins, copper proteins, and the like, obtained from animals, plants and microorganisms. The isoelectric points of these colored proteins are required to be determined correctly in advance of operation. The pHs of isoelectric point markers used in this invention are preferably in the range of from 3.9 to 10.6.

Typical colored proteins are shown in Table 1. For the accurate determination of a pH gradient appearing in a gel after electrophoresis, isoelectric point markers according to invention comprise at least two colored proteins of which the isoelectric points pH's are known, and wherein the difference between the highest value and the lowest value among the isoelectric points of the said proteins is not less than 0.5.

TABLE 1

| Proteins | Type | Source | Isoelectric point at 0-2° C |
|---|---|---|---|
| Cytochrome-c | Oxidized | Horse | 10.6 |
| Cytochrome-c$_2$ | Reduced | *Rhodopsuedomonas palustris* | 10.0 |
| Myoglobin | — | Sperm whale | 8.1 |
| Hemoglobin | — | Rat | 7.5 |
| Myoglobin | — | Horse | 7.3 |
| Cytochrome-c$_2$ | Reduced | *Rhodospirillum rubrum* | 6.2 |
| Cytochrome-c$_2$ | Reduced | *Rhodopseudomonas spheroides* | 5.8 |
| Cytochrome-c' | Oxidized | *Rhodospirillum rubrum* | 5.6 |
| Cytochrome-c' | Oxidized | *Rhodopseudomonas spheroides* | 5.0 |
| Cytochrome-c$_{551}$ | Oxidized | *Pseudomonas aeruginosa* | 4.7 |
| Acetylated Cytochrome-c | — | Horse | 3.9 |

Depending on the purpose of the application, a combination or set of more than two proteins, the isoelectric points of which are differently less than 0.5, may be used, if the difference between the highest value and the lowest value among the isoelectric points of the proteins is not less than 0.5.

When isoelectric point markers comprising the colored proteins listed in Table 1 are examined along with samples by conventional gel isoelectric separation method, each marker appears as a colored band at the position of inherent isoelectric point. Consequently, each colored band presents its own position at a look without any complex operation and the pH gradient in the gel is easily determined by means of each isoelectric point and position.

The analysis of proteins by using the said isoelectric point markers is carried out in the following procedures. In case that isoelectric points of proteins to be assayed are known in advance, the positions of the proteins are determined according to the pH gradient in the gel which was previously obtained by the isoelectric point markers of this invention. Therefore the portions including the proteins are removed and then the extracted proteins are assayed. On the other hand, in case that isoelectric points of proteins to be assayed are not known, the pH gradient in the gel is determined by the isoelectric point markers of the invention and the positions of proteins in the gel are separately determined by staining the proteins or by measuring the activities of the proteins extracted from sliced gel portion. Thus the isoelectric point of the protein is obtained.

It is not always required to feed the isoelectric point markers along with samples. It may be possible to feed the isoelectric point markers into one gel column (Standard Column) and to feed samples into separate gel columns which are then separated with Standard Column. This procedure is very convenient, when a number of samples are determined at the same time.

As mentioned above, the isoelectric separation of proteins by using the isoelectric point markers according to this invention can simplify the determination of isoelectric point greatly. This invention provides the advantage that a lot of samples can be measured in a short time, reduces the possibility that proteins are denaturalized in the pH determination, and makes it possible that the activity of a protein is measured more precisely. Therefore this invention may bring about the increased prevalence of the isoelectric separation method.

EXAMPLE 1

A combination of isoelectric point markers such as cytochrome c from Rhodopseudomonas spheroides (oxidized, pI = 5.0), cytochrome c' from Rhodospirillum rubrum (oxidized, pI = 5.6), cytochrome $c_2$ from Rhodospirillum rubrum (reduced, pI = 5.8), myoglobin from horse (pI = 7.5), myoglobin from sperm whale (pI = 8.1) was used in the gel isoelectric separation of isoenzymes of pyruvate kinase extracted from the rat liver.

A gel columm was prepared in the following manner. 1.2 g of acrylamide, 60 mg of N,N'-methylene bisacrylamide, 0.012 mg of riboflavin, 0.135 ml of N,N,N',N'-tetramethylethylenediamine, 5 mg of ammonium persulfate and 1.2 ml of 40% Ampholine (a trade name of product by LKB Co., Ltd. in Sweden) aqueous solution (pH 3.5 –10) were dissolved in pure water and the total volume of the solution was adjusted to 24 ml. The resulting solution was blended thoroughly in a flask, deaerated in an aspirating desiccator and then fed into a glass column (5 × 100 mm) up to about 70 mm high. Finally photopolymerization was conducted.

The sample solution was prepared in the following manner. The rat liver was crushed and blended with EDTA, mercaptoethanol and Tris-HCl buffer. The supernatant was separated from the mixture by centrifugation (105,000 × g). 14 μl of the solution (equivalent to 7 mg of the liver) was used as the sample solution.

10 μl of a solution containing 20 μg each of the said isoelectric point markers and 24 μl of Ampholine glycerine solution (60% of glycerine solution containing 4% of Ampholine (pH 3.5–10) were added to 14 μl of the said sample solution. Thereafter the resulting mixture was injected into the said gel column gently to form a sample layer. Above the sample layer, 50 μl of protective layer comprising 15% of glycerine and 2% of Ampholine (pH 3–6) was overlayed.

The bottom of the resulting gel column was dipped in the anode solution comprising 1 M aqueous solution of NaOH and the reverse side was dipped in the cathode solution comprising 0.02 M aqueous solution of phosphoric acid. Thereafter electrophoresis was carried out at the constant voltage of 200 V and for 5 hours. During the application, the column was kept at 0°–1° with cooling water.

As soon as electrophoresis endedd, the gel was taken out of the column. Thereafter determining the positions of the isoelectric point markers by sight, a figure of pH gradient was drawn by means of isoelectric points of the markers and their positions. (FIG. 1)

The gel was sliced equally into 28 pieces at the interval of 2.5 mm and each piece was added to 0.3 ml of 0.1 M Tris-HCl buffer solution containing 5mM of EDTA and 10 mM of β-mercaptoethanol and homogenized. The supernatant was separated from the homogenized mixture by centrifugatiomn (3,000 × g) for 15 minutes and its pyruvate kinase activity was assayed.

Figure 2:
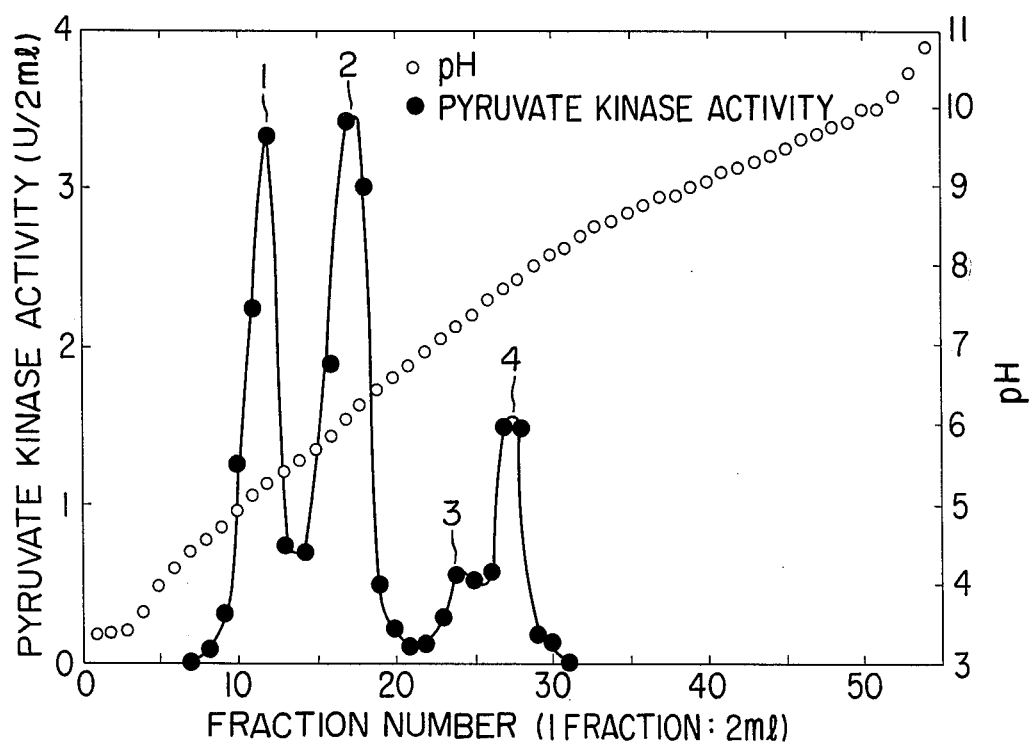
FIG. 2 is a chart showing the result obtained by using a conventional density gradient isoelectric separation method.

As the results, the pyruvate kinase from the rat liver was divided into four isoenzymes having different isoelectric points as shown in FIG. 2. According the positions showing the peaks of enzyme activity, their isoelectric points were determined to be 1(pI=5.5), 2(pI=6.2), 3(pI=7.3), 4(pI=7.6).

These values were accorded with the values of isoelectric points obtained by means of the density gradient isoelectric separation method in a gel-free solution as mentioned hereinafter.

REFERENCE EXAMPLE

A density gradient isoelectric separation was conducted by using 110 ml of separation column made by LKB Co., Ltd. and a sample of rat liver extract prepared by the same manners as in Example 1.

Ampholine (pH 3.5–10) was used in a similar manner as in Example 1. Ampholine was added to 2.1 ml of the sample solution with sucrose solution and the resulting mixture was charged into the said column to form the predetermined density gradient, the concentration of Ampholine and sucrose being to be 1.5% and 50% respectively in the bottom of the column, to be 0.5% and 0% respectively in the top of the column and the average concentration of Ampholine through the column being to be 1.0%.

A concentrated phosphoric acid solution and a 1% solution of ethylenediamine were used as the anode solution and cathode solution respectively. An electric current was applied at the voltage of 600 V and for 40 hours along with cooling the column to maintain at 0°–2° C.

As soon as the electrophoresis ended, the solution in the column was discharged through the fraction nozzle placed at the bottom of the columm and fractionated at 2 ml each. The pH value of each fraction was measured by means of a digital pH meter made by Beckman and the pyruvate kinase activity of each fraction was assayed.

As the results, four isoenzymes were separated as shown in FIG. 2. The isoelectric points of these isoenzymes are 1(pI=5.3), 2(pI=6.2), 3(pI=7.2), 4(pI=7.8).

What is claimed is:

1. Isoelectric point markers for a gel isoelectric separation, which comprise at least two colored proteins of which the isoelectric point pHs are known, and wherein the difference between the highest value and the lowest value among said pHs is not less than 0.5.

2. Isoelectric point markers according to claim 1, wherein the colored proteins are cytachrome-cs, myoglobins, hemoglobins, flavoproteins, copper proteins, and the like, obtained from animals, plants and microorganisms.

3. Isoelectric point markers according to claim 1, wherein the isoelectric point pHs of the colored proteins are from 3.9 to 10.6.

4. A gel isoelectric separation method for the analysis of proteins by using isoelectric point markers which comprise at least two colored proteins of which the isoelectric point pHs are wherein the difference between the highest value and the lowest value among the said pHs is not less than 0.5, and wherein the migration distances of the said markers are used as indicators of pH value.

5. A gel isoelectric separation method according to claim 4, wherein the colored proteins are cytochrome-cs, myoglobins, hemoglobins, flavoproteins, copper proteins and the like, various obtained from various animals, plants and microorganisms.

6. A gel isoelectric separation method according to claim 4 wherein the isoelectric point pHs of the colored proteins are from 3.9 to 10.6.

* * * * *

UNITED STATES PATENT AND TRADEMARK OFFICE
CERTIFICATE OF CORRECTION

PATENT NO. : 4,107,014
DATED : August 15, 1978
INVENTOR(S) : Yasuo Suzuki et al

It is certified that error appears in the above-identified patent and that said Letters Patent are hereby corrected as shown below:

Column 1, line 68; after "and", insert -- wherein --.

Column 6, line 4; after "are", insert -- known --.

Column 6, line 12; delete two "various" es.

Signed and Sealed this

Sixth Day of March 1979

[SEAL]

Attest:

RUTH C. MASON
Attesting Officer

DONALD W. BANNER
Commissioner of Patents and Trademarks